United States Patent [19]

Chang et al.

[11] Patent Number: 4,490,566

[45] Date of Patent: Dec. 25, 1984

[54] PRODUCTION OF PHENOL

[75] Inventors: Clarence D. Chang, Princeton; Bruce P. Pelrine, Lawrenceville, both of N.J.

[73] Assignee: Mobil Oil Corporation, New York, N.Y.

[21] Appl. No.: 492,104

[22] Filed: May 6, 1983

[51] Int. Cl.$^3$ ................................................ C07C 37/08
[52] U.S. Cl. ..................... 568/798; 568/385; 568/741; 568/754; 568/768
[58] Field of Search .............. 568/385, 485, 741, 754, 568/768, 798

[56] References Cited

U.S. PATENT DOCUMENTS

| | | | |
|---|---|---|---|
| 3,305,590 | 2/1967 | Pollitzer et al. | 568/768 |
| 3,308,069 | 3/1967 | Wadlinger et al. | 423/328 |
| 3,702,886 | 11/1972 | Arguer et al. | 423/328 |
| 3,709,979 | 1/1973 | Chu | 423/328 |
| 3,832,449 | 8/1974 | Rosinski et al. | 423/328 |
| 3,978,141 | 8/1976 | Jouffret | 568/798 |
| 4,016,218 | 4/1977 | Haag et al. | 423/328 |
| 4,016,245 | 4/1977 | Plank et al. | 423/328 |
| 4,046,859 | 9/1977 | Plank et al. | 423/328 |
| 4,229,424 | 10/1980 | Kokotailo | 423/328 |
| 4,246,203 | 1/1981 | Wirth | 568/798 |
| 4,273,623 | 1/1981 | Hashimoto et al. | 568/768 |
| 4,375,575 | 3/1983 | Slaugh | 585/480 |

OTHER PUBLICATIONS

Frillette et al., "J. Catalysis", vol. 67, (1981), pp. 218–222.
Zh. Prikl. Khim 54, No. 8, 1793–1799, (1981).
Z. Chem. 15 Jg. (1975), 152–153, (Heft 4).
Collection Czechoslov. Chem. Commun., vol. 40, 865–874, (1975).

Primary Examiner—Werren B. Lone
Attorney, Agent, or Firm—Alexander J. McKillop; Michael G. Gilman; Richard D. Stone

[57] ABSTRACT

Phenol and acetone are produced by the cleavage of cumene hydroperoxide in the presence of a solid heterogeneous catalyst with acidic activity comprising an intermediate pore size zeolite such as ZSM-5.

7 Claims, No Drawings

PRODUCTION OF PHENOL

FIELD OF THE INVENTION

This invention relates to the production of phenol and more particularly to a process for the production of phenol and acetone from cumene hydroperoxide.

CROSS-REFERENCE TO RELATED APPLICATIONS

Our copending U.S. patent application Ser. No. 492,093, filed May 6, 1983 (concurrently with this application) describes a process for the production of phenol and acetone using a different catalyst (zeolite beta).

BACKGROUND OF THE INVENTION

Phenol is an important organic chemical with a wide variety of industrial uses. It is used, for example, in the production of phenolic resins, this one use constituting over half the total usage, bisphenol-A, caprolactam and many other materials. A number of processes are currently in use for the production of phenol but the single process providing the largest proportion of the total production capacity is the cumene process which now accounts for over three quarters of the total U.S. production. The basic reaction involved in this process is the cleavage of cumene hydroperoxide into phenol and acetone:

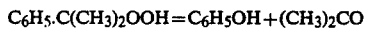

$$C_6H_5.C(CH_3)_2OOH = C_6H_5OH + (CH_3)_2CO$$

The reaction takes place under acid conditions with the yield of both phenol and acetone generally being 40 percent or more.

On the industrial scale, the cumene hydroperoxide is usually treated with dilute sulphuric acid (5 to 25 percent concentration) at a temperature of about 50° to 70° C. After the cleavage is complete, the reaction mixture is separated and the oil layer distilled to obtain the phenol and acetone together with cumene, alpha-methylstyrene, acetophenone and tars. The cumene may be recycled for conversion to the hydroperoxide and subsequent cleavage. The phenol produced in this way is suitable for use in resins although further purification is required for a pharmaceutical grade product.

Although the process described above is capable of producing both phenol and acetone in good yields, it would be desirable to find a process which would reduce the need for the product separation and purification steps which are consequent upon a homogeneous process of that kind.

The heterogenous cleavage of cumene hydroperoxide (CHP) over various acidic solids has already been reported. For example, the use of amorphous aluminosilicates for this purpose is described in J. Macromol Sci-Chem. A5(5), 995–1005, August 1971 and U.S. Pat. No. 3,305,590 describes the use of silica-alumina composites in this reaction. The use of silica-alumina gels is also described in Stud. Univ. Babes-Bolyai Ch. 16(1), 61–67(1971). Other materials whose utility as catalysts for this reaction include various zeolites such as sillimanite, as described in Zh. Prikl. Khim 54, No. 8, 1793-9 (1981) and zeolites X and Y in certain cationic forms, as reported in Z. Chem. 15 Jg. (1975) 152–153 (Heft 4). The decomposition of other peroxides over zeolites X and Y is reported in Collection Czechoslov. Chem. Commun Vol. 40, 865-874 (1975).

SUMMARY OF THE INVENTION

It has now been found that cumene hydroperoxide may be converted to phenol and acetone in good yields and with high rates of conversion and selectivity to the desired products by the use of a solid heterogenous catalyst comprising a crystalline intermediate pore size zeolite such as zeolite ZSM-5. The yields, conversions and selectivities are generally superior to those produced by the use of the large pore zeolites X and Y, especially with extended continuous operation. It is believed that this superior performance may be attributable to the greater resistance of the selected zeolites to coke precursors which otherwise would tend to deactivate the catalyst and render it less selective.

DETAILED DESCRIPTION

Feedstock

The cumene hydroperoxide starting material may be obtained in the conventional way, by oxidation of cumene in an alkaline medium, in which the hydroperoxide product is stable. Cumene, normally obtained by the alkylation of benzene with propylene, is usually emulsified in an aqueous alkaline solution such as sodium carbonate, at a pH of 8.5 to 10.5 with an emulsifying agent such as sodium stearate. Oxidation with air or oxygen at mildly elevated temperatures of about 70° to 130° C. follows, with a final conversion of about 30 percent being common. The unreacted cumene may be separated by distillation and recycled to give the cumene hydroperoxide or it may be carried through the subsequent cleavage reaction and then recycled.

Catalyst

The catalyst which is used in the present process is a solid, heterogeneous catalyst which comprises a crystalline zeolite having acidic functionality.

Many crystalline aluminosilicate zeolites are known. Some occur (at least so far) only in nature, for instance paulingite and merlinoite; some occur only as a result of synthesis, for instance zeolites A and ZSM-5; and some occur in both natural and synthetic forms, for instance mordenite, a synthetic counterpart of which is known as Zeolon, and faujasite, synthetic counterparts of which are known as zeolites X and Y. Counterparts are of course demonstrated as such by correspondence of their X-ray diffraction data, the indicia by means of which the individuality of a zeolite is established. Such data are a manifestation of the particular geometry of the three-dimensional lattice, formed of $SiO_4$ and $AlO_4$ tetrahedra crosslinked by the sharing of oxygen atoms and including sufficient cationic complement to balance the resulting negative charge on the $AlO_4$ tetrahedra, of which a zeolite consists.

The chemical formula of a zeolite is thus

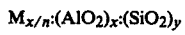

$$M_{x/n}:(AlO_2)_x:(SiO_2)_y$$

where M is a cation of valence n and x and y are the number of aluminum and silicon atoms, respectively, in the unit cell. This expression is however frequently transmuted into the mole ratio of oxides form,

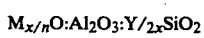

$$M_{x/n}O:Al_2O_3:Y/_{2x}SiO_2$$

which is of course empirically ascertainable and thus the only formula which can be ascribed to a zeolite when its unit cell contents are unknown. Since the only significant quantity in such a formula is the term y/2x, and since this term (which is almost invariably a range) can usually be satisfied by many zeolites of widely differing lattice geometry, chemical formula is not of value in establishing the identity of a zeolite. Furthermore, such a formula frequently expresses artefact when empirically derived, the cationic-valence-aluminum-atoms ratio deviating from the unity which it must in fact be; and it fails to provide for zeolites whose lattice structure can be brought into existence from reaction mixtures from which alumina is excluded.

The zeolite catalysts which are used in the present process enable the CHP to be cleaved to acetone and phenol at high conversions and with good selectivity, even at high space velocities. The zeolites which are used according to the present invention are the so-called intermediate pore size zeolites, that is, zeolites which are characterized by a Constraint Index of 1 to 12 and a silica:alumina ratio of at least 12:1.

The significance of the Constraint Index of a zeolite is described in J. Catalysis 67, 218-222 (1981), together with details of the method by which it may be determined and examples of its value in some typical zeolites; details of the method by which it may be determined are also given in U.S. Pat. No. 4,016,218, to which reference is made for these details.

Because constraint index is related to the crystalline structure of the zeolite but is nevertheless determined by means of a test which exploits the capacity of the zeolite to engage in a cracking reaction, that is, a reaction dependent upon the possession of acidic sites and functionality in the zeolite, the sample of zeolite used in the test should be representative of the zeolitic structure whose constraint index is to be determined and should also posses requisite acidic functionality for the test. Acidic functionality may, of course, by varied artifices including base exchange, steaming or control of silica:alumina ratio.

The silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed.

Zeolites which conform to the specified values of Constraint Index and silica:aluumina ratio include the zeolites ZSM-5, ZSM-11, ZSM-12, ZSM-23, ZSM-35, ZSM-38, the ZSM-5/ZSM-11 intermediate, and ZSM-48 which are described, respectively, in U.S. Pat. Nos. 3,702,886, 3,709,979, 3,832,449, 4,076,842, 4,016,245, 4,046,859, 4,229,424 and 4,375,573 (also U.S. application Ser. No. 303,276, filed Sept. 17, 1981), to which reference is made for details of these zeolites. These zeolites may be produced with differing silica:alumina ratios ranging from 12:1 upwards. They may, in fact, be produced from reaction mixtures from which aluminum is intentionally excluded, so as to produce materials having extremely high silica:alumina ratios which, in theory at least may extend up to infinity. Silica:alumina ratios of at least 30:1 and higher will be common for these zeolites, e.g. 70:1, 200:1, 500:1, 1600:1 or even higher. Highly siliceous forms of zeolites ZSM-5, ZSM-11 and ZSM-12 are described, respectively, in U.S. Pat. No. Re. 29,948 and European Patent Publication No. 14,059 to which reference is made for details of these zeolites.

Because the present process is acid-catalyzed, the extent of acidic activity possessed by the catalyst will govern both the yield and the speed of the reaction. The acidity of the zeolites may, as mentioned above, be conveniently controlled in a number of different ways, for example, by base exchange, by steaming or by control of the silica:alumina ratio of the zeolite. Base exchange with alkali metals particularly sodium will tend to reduce the acidity of zeolites in the hydrogen form because the acidic protons become replaced with sodium ions. Conversely, alkali metal forms of the zeolite may be converted to the more acidic hydrogen form by ammonium base exchange followed by calcination. Either kind of exchange may, of course, be complete or partial in order to achieve the desired variation in acid acitivity. Steaming is generally effective to reduce activity by removal of the aluminum active sites, although certain zeolites respond more to this treatment than others. Control of silica/alumina ratio affects acidic activity by controlling the proportion of $AlO_4$ tetrahedra in the zeolite which are available for protonation; high silica zeolites therefore tend to have lower acidic activity than those with lower silica:alumina ratios. For the purposes of the present process, it is preferred to use a catalyst with an acidity, measured by alpha value, from 5 to 1000, preferably 10 to 500. The significance of the alpha value and a method for its determination are described in U.S. Pat. No. 4,016,218, to which reference is made.

The zeolite may be catalytically inactive when prepared in the presence of organic cations, possibly because the intracrystallin free space is occupied by organic cations from the forming solution. The zeolite may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite; however, the presence of these cations does appear to favor their formation. More generally, it is desirable to activate this type catalyst by base exchange with ammonium salts followed by calcination in air at about 540° C. for from about 15 minutes to 24 hours.

It may be desirable to incorporate the zeolite in another material resistant to the temperatures and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families. Such clays can be used in the raw state as originally mined or initially subjected to calcination, acid treatment or chemical modification.

The zeolite may also be composited with a porous matrix material, such as silica-alumina, silica-magnesia, silica-zornia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite and inorganic oxide gel matrix may typically vary with the zeolite content ranging from 1 to 99, and more usually from 5 to 80 percent by weight of the composite.

Reaction Conditions

The cleavage reaction may conveniently be carried out in the liquid phase at elevated temperatures, usually at a temperature from 50° C., preferably 80° to 120° C. The reaction proceeds readily at temperatures within this range, without undue production of undesired by-products such as alpha-methylstyrene and acetophenone. However, if greater amounts of these materials can be tolerated, higher temperatures, for example, up to 200° C. may be used although care should be taken to prevent temperature excursions caused by the exothermic nature of the reaction. Temperatures of approximately 100° C. are preferred in order to obtain adequate reaction speed and to avoid by-product formation.

The cumene hydroperoxide is preferably dissolved in a solvent such as benzene, toluene, acetone, cumene, or another hydrocarbon which is inert to the reaction. Alternatively, and somewhat less desirably, the cumene hydroperoxide may be suspended in an inert solvent such as an aliphatic hydrocarbon or a halocarbon. The use of a solvent is particularly preferred because intimate contact with the catalyst will be assured and, in addition, evaporation of the solvent will assist in dissipating the heat of the reaction (about 60 KCal/mole). The temperature of the reaction may therefore be controlled at least to some degree by controlling the circulation rate of the reaction solution. A volatile suspension medium offers similar advantages except that close contact with the catalyst is not so readily assured.

The reaction, being a liquid phase reaction, is preferably conducted in a fixed bed or a slurry reactor. If a fixed bed is used, the exotherm can be controlled by the circulation rate over the bed, with rates of 1 to 100, preferably 10 to 50 WHSV having been found suitable. It may be preferable further to operate with a diluted catalyst, e.g. a catalyst in a non-acidic, inert matrix or supported on an inert support. Alternatively, a slurry reactor may be used, with a solution of the cumene hydroperoxide flowing vertically upwards through the catalyst bed at a sufficient velocity to maintain the bed in an ebullient state. This form of operation will be favored because the efficient thermal transfer within the bed promotes uniformity of conditions within the bed. Control of the exotherm may also be effected by permitting the solvent to evaporate from the bed, after which it may be recycled.

Extremely high conversions, frequently of 100 percent, of the cumene hydroperoxide may be obtained by the present process, accompanied by good selectivity to the desired phenol and acetone products. In this respect, the present process is superior to that of the known processes which make significant amounts of methylstyrene, acetophenone, 2-phenyl-propan-2-ol and 4-cumyl phenol as by-products. In addition, the use of a solid, heterogeneous catalyst facilitates product recovery as there is no acid to separate from the reaction products or to dispose of afterwards.

The invention is illustrated in the following Examples. All percentages, parts and proportions are by weight.

EXAMPLE 1

A small scale batch process was carried out by adding 0.5 g. HZSM-5 (silica:alumina ratio 70, alpha value 140) to a solution of 0.375 g. cumene hydroperoxide (CHP) in 25 ml. benzene in a 100 ml round bottom flask at room temperature.

The reaction mixture was then stirred for about 3 hours after which the autocatalytic reaction appeared complete, with a final temperature of 60° C. The final conversion to phenol was 100 percent by gas chromatograph.

EXAMPLES 2-4

A vertically disposed downflow reactor containing 3 ml. of the catalyst being tested was connected for the CHP feed to be supplied at the top with product removal at the bottom. Temperature control was arranged by external heating jacket with an internal temperature monitor in the bed. Product analysis was by gas chromatograph.

The feed composition is shown in Table 1 below.

TABLE 1

| Feed Composition | |
|---|---|
| | Weight Percent |
| Cumene hydroperoxide (CHP) | 79.67 |
| Cumene | 11.04 |
| 2-Phenyl-2-propanol | 6.47 |
| Acetophenone | 2.56 |
| Alpha-methyl styrene | 0.26 |
| | 100.00 |

The catalysts used were as follows:
Example 2: HZSM-5 (silica:alumina ratio 70, alpha value 140)
Example 3: Zeolite ZK-5 (alpha value 15)
Example 4: Quartz chips ("Vycor"-trademark)
The ZK-5 zeolite (small pore zeolite and the quartz chips used in Example 4 are used for purposes of comparison.

The results are shown in Tables 2 to 4 below in terms of the product distribution, selectivity to phenol and acetone and CHP conversion after varying times on stream. The temperatures at these times are also indicated. The superiority of the ZSM-5 catalyst is apparent from the figures for conversion and selectivity.

TABLE 2

| | Example 2 - HZSM-5 | | | | | | | | | |
|---|---|---|---|---|---|---|---|---|---|---|
| Time (hrs.) | 0.62 | 1.10 | 1.47 | 1.87 | 2.20 | 2.78 | 3.38 | 3.93 | 4.63 | 5.7 |
| Temp (°C.) | 53 | 58 | 63 | 70 | 167 | 167 | 167 | 152 | 141 | 141 |
| Product Dist.: | | | | | | | | | | |
| Acetone | — | — | 1.38 | 6.40 | 16.31 | 14.07 | 15.37 | 16.50 | 23.84 | 28.33 |
| Cumene | 10.82 | 11.22 | 14.85 | 10.96 | 14.03 | 13.33 | 13.16 | 13.67 | 15.01 | 14.13 |
| a-Methyl Styrene | 1.46 | 1.13 | 1.09 | 0.77 | 25.68 | 28.27 | 27.73 | 26.20 | 28.13 | 14.44 |
| Acetophenone | 0.10 | 2.34 | 3.64 | 3.47 | 13.12 | 14.95 | 13.96 | 12.44 | 6.34 | 3.80 |

TABLE 2-continued

| | Example 2 - HZSM-5 | | | | | | | | | |
|---|---|---|---|---|---|---|---|---|---|---|
| Time (hrs.) | 0.62 | 1.10 | 1.47 | 1.87 | 2.20 | 2.78 | 3.38 | 3.93 | 4.63 | 5.7 |
| Temp (°C.) | 53 | 58 | 63 | 70 | 167 | 167 | 167 | 152 | 141 | 141 |
| 2-Phenyl-2-Propanol | 4.89 | 4.01 | 3.65 | 2.78 | 1.35 | 1.47 | 1.35 | 1.40 | 0.67 | 0.55 |
| Phenol | 1.34 | 3.79 | 6.42 | 8.52 | 28.15 | 26.59 | 27.32 | 28.80 | 24.94 | 38.61 |
| CHP | 81.39 | 77.50 | 68.97 | 67.10 | 0.14 | — | — | — | — | — |
| Unknown | — | — | — | — | 1.22 | 1.31 | 1.11 | 0.98 | 1.08 | 0.14 |
| Acetone:Phenol | — | — | 0.21 | 0.75 | 0.58 | 0.53 | 0.56 | 0.57 | 0.96 | 0.73 |
| Selectivity | 31.50 | 78.10 | 57.70 | 91.80 | 52.50 | 48.0 | 50.30 | 53.50 | 57.10 | 78.20 |
| CHP Conversion | 0 | 2.70 | 13.40 | 15.80 | 99.80 | 100 | 100 | 100 | 100 | 100 |

TABLE 3

| | Example 3 - Zeolite ZK-5 | | | | | | |
|---|---|---|---|---|---|---|---|
| Temp (°C.) | 80 | 80 | 80 | 185 | 191 | 140 | 130 |
| Time (hrs.) | 1.27 | 2.57 | 2.83 | 3.55 | 3.80 | 4.23 | 4.63 |
| Product Dist.: | | | | | | | |
| Acetone | 3.76 | 2.46 | 3.42 | 27.49 | 20.75 | 19.56 | 22.92 |
| Cumene | 16.33 | 13.75 | 16.15 | 15.08 | 12.51 | 11.96 | 12.14 |
| a-Methyl Styrene | 1.18 | 0.93 | 1.21 | 19.84 | 26.54 | 24.23 | 18.93 |
| Acetophenone | 2.50 | 2.19 | 3.68 | 3.17 | 8.96 | 14.89 | 9.51 |
| 2-Phenyl-2-Propanol | 7.16 | 5.04 | 6.00 | 0.31 | 0.13 | 0.47 | 0.65 |
| Phenol | 4.68 | 3.65 | 4.25 | 33.75 | 30.26 | 27.90 | 31.59 |
| CHP | 64.38 | 71.98 | 65.29 | — | — | 0.33 | 3.86 |
| Unknown | — | — | — | 0.36 | 0.85 | 0.65 | 0.40 |
| Acetone:Phenol | 0.80 | 0.67 | 0.80 | 0.81 | 0.69 | 0.70 | 0.73 |
| Selectivity | 55.00 | 64.40 | 51.60 | 71.40 | 59.30 | 55.60 | 66.80 |
| CHP Conversion | 19.20 | 9.70 | 18.00 | 100 | 100 | 99.60 | 95.20 |

TABLE 4

| | Example 4 - Quartz | | | | | | |
|---|---|---|---|---|---|---|---|
| Temp (°C.) | 76 | 110 | 198 | 235 | 235 | 120 | 121 |
| Time (hrs.) | 0.38 | 0.90 | 1.33 | 4.40 | 4.58 | 5.53 | 5.83 |
| Product Dist.: | | | | | | | |
| Acetone | 0.08 | 0.08 | 3.47 | 5.73 | 3.28 | 0.21 | — |
| Cumene | 13.69 | 9.64 | 20.30 | 12.71 | 11.72 | 17.48 | 14.39 |
| a-Methyl Styrene | 0.52 | 0.25 | 7.16 | 28.55 | 25.47 | 1.15 | — |
| Acetophenone | 2.57 | 2.65 | 21.35 | 30.30 | 43.00 | 3.94 | 3.18 |
| 2-Phenyl-2-Propanol | 7.11 | 6.95 | 20.29 | 8.20 | 7.94 | 8.88 | 8.04 |
| Phenol | 0.06 | 0.38 | 1.57 | 2.92 | 4.66 | 0.53 | — |
| CHP | 75.95 | 80.05 | 25.33 | 11.07 | 0.29 | 67.81 | 74.39 |
| Unknown | — | — | 0.52 | 0.53 | 3.65 | — | — |
| Acetone:Phenol | 1.33 | 0.21 | 2.21 | 1.96 | 0.70 | 0.40 | — |
| Selectivity | 3.80 | 0.30 | 9.30 | 12.60 | 10.00 | 6.20 | 0 |
| CHP Conversion | 4.60 | 0 | 68.20 | 86.10 | 99.60 | 14.90 | 6.60 |

EXAMPLE 5

HZSM-5 (0.5 cc., silica:alumina ration 70:1, alpha=140) was mixed with 5 cc quartz chips ("Vycor") and used for the cleavage of CHP in a vertical, downflow reactor at a temperature of 100° C., at different space velocities varying from 4 to 56 LHSV.

The compositions of the feed and of the products obtained at the different space velocities are shown in Table 5 below.

TABLE 5

| | CHP Conversion over HZSM-5 | | | | | |
|---|---|---|---|---|---|---|
| Feed | | | | | | |
| — | Acetone | 28.3 | 20.1 | 11.5 | 5.5 | 3.2 |
| 9.0 | Cumene | 12.1 | 12.5 | 12.5 | 12.1 | 14.2 |
| 0.3 | a-Methylstyrene | 1.4 | 0.9 | 0.9 | 1.0 | 0.8 |
| 2.1 | Acetophenone | 2.1 | 2.0 | 2.1 | 1.9 | 1.7 |
| 6.0 | 2-Phenyl-2-Propanol | 0.5 | 1.2 | 2.4 | 3.3 | 3.9 |
| — | Phenol | 49.6 | 34.2 | 18.6 | 9.9 | 5.6 |
| 82.6 | CHP | 6.0 | 29.1 | 52.0 | 66.3 | 70.6 |
| | LHSV, hr$^{-1}$ | 4 | 8 | 15.7 | 38 | 56 |
| | Temperature, °C. | 100 | 100 | 100 | 100 | 100 |
| | Acetone/Phenol | 0.57 | 0.59 | 0.62 | 0.57 | 0.56 |
| | CHP Conversion | 92.7 | 64.8 | 37.0 | 19.7 | 14.5 |
| | Acetone-Phenol Selectivity | 94.9 | 93.0 | 88.0 | 80.2 | 60.6 |

EXAMPLE 6

A sample of zeolite Y in the hydrogen from (0.5 cc) was mixed with 5 cc quartz chip ("Vycor") and used for the cleavage of CHP in a vertical, downflow reactor at a temperature of 100° C. as different space velocities varying from 16 to 84 LHSV.

The compositions of the feed and of the products obtained at the different space velocities are shown in Table 6 below. Comparison with Table 5 shows the superior selectivity under most conditions of the ZSM-5 catalyst.

TABLE 6

| | CHP Conversion over HY | | | | |
|---|---|---|---|---|---|
| Feed | | | | | |
| —.4 | Acetone | 7.3 | 3.3 | 2.0 | 1.4 |
| 14.3 | Cumene | 18.8 | 18.9 | 15.4 | 14.9 |
| — | a-Methylstyrene | 1.1 | 1.0 | 0.2 | 0.2 |
| 1.2 | Acetophenone | 1.7 | 1.1 | 1.4 | 1.2 |
| 5.7 | 2-Phenyl-2-Propanol | 3.2 | 4.5 | 5.1 | 5.0 |
| 1.6 | Phenol | 14.6 | 6.7 | 4.6 | 3.4 |
| 77.0 | CHP | 53.3 | 64.5 | 71.4 | 74.2 |
| | LHSV, hr$^{-1}$ | 16 | 35 | 56 | 84 |
| | Temperature, °C. | 100 | 100 | 100 | 100 |
| | Acetone/Phenol | 0.53 | 0.57 | 0.53 | 0.56 |
| | CHP Conversion | 30.8 | 16.2 | 7.3 | 3.6 |
| | Acetone-Phenol Selectivity | 76.5 | 58.8 | 75.4 | 77.8 |

We claim:

1. A process for the production of phenol and acetone which comprises contacting cumene hydroperoxide with a catalyst comprising a crystalline zeolite having a Constraint Index of 1 to 12 and a silica:alumina ratio of at least 12:1.

2. A process according to claim 1 in which the zeolite is at least partly in the hydrogen form.

3. A process according to claim 1 in which the zeolite is ZSM-5, ZSM-11, ZSM-23, ZSM-35 or ZSM-38.

4. A process according to claim 1 in which the zeolite is ZSM-5.

5. A process according to claim 4 in which the zeolite has a silica:alumina ratio of at least 70:1.

6. A process according to claim 1 in which the cumene hydroperoxide is contacted with the zeolite at a temperature of 80° C. to 200° C.

7. A process according to claim 1 in which the cumene hydroperoxide is contacted with the zeolite at a temperature of 80° C. to 120° C.

* * * * *